US005780630A

United States Patent [19]
Lyga

[11] Patent Number: 5,780,630
[45] Date of Patent: Jul. 14, 1998

[54] INTERMEDIATE USEFUL IN THE SYNTHESIS OF PESTICIDAL URACILS

[75] Inventor: John W. Lyga, Basking Ridge, N.J.

[73] Assignee: FMC Corporation, Philadelphia, Pa.

[21] Appl. No.: 866,363

[22] Filed: May 30, 1997

Related U.S. Application Data

[60] Provisional application No. 60/025,815, Aug. 30, 1996.
[51] Int. Cl.$^6$ ............................................. C07D 239/557
[52] U.S. Cl. ............................................................ 544/309
[58] Field of Search ................................................ 544/309

[56] References Cited

U.S. PATENT DOCUMENTS 5,683,966  11/1997  Konz ........................................ 504/243

*Primary Examiner*—Patricia L. Morris
*Attorney, Agent, or Firm*—Woodcock Washburn Kurtz Mackiewicz & Norris, LLP

[57] ABSTRACT

The compound 1-methyl-6-trifluoromethyl-2,4(1H,3H)-pyrimidinedione is a novel compound useful in the preparation of pesticidal uracils. A route to the compound is disclosed, as is its use to prepare a known herbicide.

1 Claim, No Drawings

INTERMEDIATE USEFUL IN THE SYNTHESIS OF PESTICIDAL URACILS

This application claims priority to U.S. Provisional application Ser. No. 60/025,815 filed Aug. 30, 1996.

This application relates to the preparation of a key intermediate in the synthesis of pesticidal uracils, for example, uracil herbicides. A number of active herbicides containing the 1-methyl-6-trifluoromethyl-2,4(1H,3H)-pyrimidinedione moiety are known, including 1-methyl-3-(2,5-dichloro-3-methoxyphenylmethyl)-6-trifluoromethyl-2,4(1H,3H)-pyrimidinedione. The synthesis of this herbicide by use of the intermediate of this invention is illustrated below.

A route to the novel intermediate is represented by the following equations:

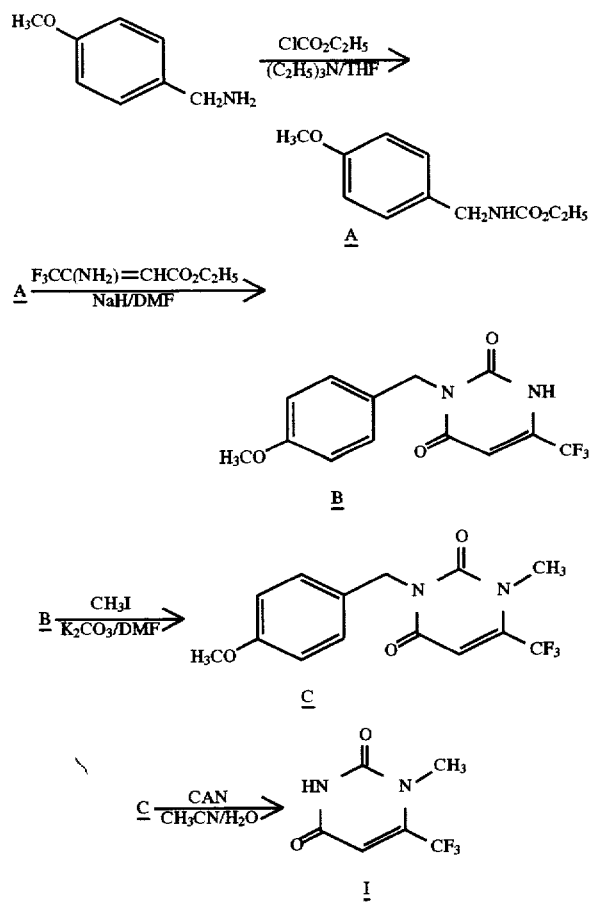

in which THF is tetrahydrofuran, DMF is N,N-dimethylformamide, and CAN is ammonium cerium(IV) nitrate.

In this sequence a 4-alkoxyphenylmethylamine is reacted with an alkyl chloroformate under mildly basic conditions to yield an alkyl (4-alkoxyphenyl-methyl)carbamate. This intermediate is then reacted with an alkyl 3-amino-4,4,4-trifluoro-2-butenoate to yield 6-trifluoromethyl-3-(4-alkoxyphenyl-methyl)-2,4(1H,3H)-pyrimidinedione. Following methylation with methyl iodide under basic conditions, the 3-substituent on the pyrimidine ring is removed by reaction with ammonium cerium(IV) nitrate to yield the desired 1-methyl-6-trifluoromethyl-2,4(1H,3H)-pyrimidinedione (I). This synthesis is exemplified in Example 1.

The desired pesticide may then be prepared by reacting the appropriate halide of the 3-substituent to be introduced. Such a synthesis is exemplified in Example 2.

EXAMPLE 1
SYNTHESIS OF 1-METHYL-6-TRIFLUOROMETHYL-2,4(1H,3H)-PYRIMIDINEDIONE, A SYNTHESIS INTERMEDIATE

Step A
Synthesis of Ethyl (4-methoxyphenylmethyl)carbamate as an Intermediate A stirred solution of 6.0 mL (0.046 mole) of 4-methoxyphenylmethyl-amine and 6.5 mL (0.047 mole) of triethylamine in 200 mL of tetrahydrofuran was cooled to about 5° C., and a solution of 4.4 mL (0.046 mole) of ethyl chloroformate in 10 mL of tetrahydrofuran was added. Upon completion of the addition the reaction mixture was allowed to warm to ambient temperature, then was poured into a mixture of 200 mL of ice and 200 mL of an aqueous solution saturated with ammonium chloride. This mixture was extracted with 300 mL of diethyl ether, and the extract was dried with magnesium sulfate and filtered. The filtrate was concentrated under reduced pressure, yielding 4.2 grams (43.8% yield) of ethyl (4-methoxyphenylmethyl)-carbamate. The NMR spectrum was consistent with the proposed structure.

Step B
Synthesis of 6-trifluoromethyl-3-(4-methoxyphenylmethyl)-2,4(1H,3H)-pyrimidinedione as an Intermediate Sodium hydride (60% in mineral oil), 0.88 gram (0.02 mole), was washed with two 10 mL portions of heptane, then stirred with 50 mL of N,N-dimethylformamide. The mixture was cooled to 0°–5° C., and a solution of 3.7 grams (0.02 mole) of ethyl 3-amino-4,4,4-trifluoro-2-butenoate in 10 mL of N,N-dimethylformamide was added dropwise. Upon cessation of the evolution of hydrogen gas a solution of 4.2 grams (0.02 mole) of ethyl (4-methoxy-phenylmethyl)carbamate in 10 mL of N,N-dimethylformamide was added, and the reaction mixture was heated to 90° C., where it stirred for about one hour. After this time the reaction mixture was cooled and poured into 500 mL of ice and aqueous 10% hydrochloric acid. The resultant solid was collected by filtration and dried, yielding 4.1 grams (68.3% yield) of 6-trifluoro-methyl-3-(4-methoxyphenylmethyl)-2,4(1H,3H)-pyrimidinedione; mp 203°–204° C. The NMR spectrum was consistent with the proposed structure.

Step C
Synthesis of 1-methyl-6-trifluoromethyl-3-(4-methoxyphenyl-methyl)-2,4(1H,3H)-pyrimidinedione as an Intermediate A solution of 3.0 grams (0.01 mole) of 6-trifluoromethyl-3-(4-methoxy-phenylmethyl)-2,4(1H,3H)-pyrimidinedione in 25 mL of N,N-dimethylform-amide was stirred and 1.4 grams (excess) of potassium carbonate was added. To this was then added 0.7 mL (0.01 mole) of methyl iodide. Upon completion of the addition the reaction mixture was stirred at ambient temperature for about 18 hours, then poured into a mixture of 100 mL of ice and 100 mL of aqueous 10% hydrochloric acid. The resultant solid was collected by filtration and washed with water. The solid was then dissolved in 200 mL of ethyl acetate and dried with magnesium sulfate. The mixture was filtered and the filtrate concentrated under reduced pressure, yielding 2.1 grams (66.9% yield) of 1-methyl-6-trifluoromethyl-3-(4-methoxyphenylmethyl)-2,4(1H,3H)-pyrimidinedione, mp 79°–80° C. The NMR spectrum was consistent with the proposed structure.

Step D
Synthesis of 1-methyl-6-trifluoromethyl-2,4(1H,3H)-pyrimidine-dione as a Synthesis Intermediate to Pesticidal Uracils To a stirred mixture of 14.5 grams (0.046 mole) of 1-methyl-6-trifluoro-methyl-3-(4-methoxyphenylmethyl)-2,4(1H,3H)-pyrimidinedione and 50 mL of water in 200 mL of acetonitrile was added 30 grams (0.055 mole) of ammonium cerium(IV) nitrate. The reaction mixture was stirred at ambient temperature for about two hours, and an additional 20 grams (0.034 mole) of ammonium cerium(IV) nitrate was added. Upon completion of the addition the reaction mixture was stirred at ambient temperature for about 18 hours, then partitioned in 200 mL of water and 300 mL of ethyl acetate. The aqueous layer was separated and washed with two 100 mL portions of ethyl acetate. The washes and organic layer were combined and washed with one 100 mL portion of aqueous saturated sodium chloride solution. The organic layer was dried with magnesium sulfate and filtered. The filtrate was concentrated under reduced pressure to a solid residue, which was triturated with 1:1-petroleum ether:diethyl ether. The solid was collected by filtration, washed with diethyl ether, and dried, yielding 4.1 grams (46% yield) of 1-methyl-6-trifluoromethyl-2,4(1H,3H)-pyrimidinedione; mp 146°–147° C. The NMR spectrum was consistent with the proposed structure.

Elemental Analysis Calculated for $C_6H_5F_3N_2O_2$

| Element | % Theoretical | % Found |
| --- | --- | --- |
| Carbon | 37.13 | 37.16 |
| Hydrogen | 2.60 | 2.62 |
| Nitrogen | 14.43 | 14.32 |

EXAMPLE 2

SYNTHESIS OF 1-METHYL-3-(2,5-DICHLORO-3-METHOXYPHENYL-METHYL)-6-TRIFLUOROMETHYL-2,4(1H,3H)-PYRIMIDINEDIONE, A KNOWN URACIL HERBICIDE

Under a nitrogen atmosphere, a solution of 0.11 gram (0.0006 mole) of 1-methyl-6-trifluoromethyl-2,4(1H,3H)-pyrimidinedione in 1.2 mL of anhydrous tetrahydrofuran was stirred, and 1.38 mL (0.0014 mole) of tetrabutyl ammonium fluoride (1M in tetrahydrofuran), followed by 0.10 gram (0.0004 mole) of 2,5-dichloro-5-methoxyphenylmethyl bromide, were added via syringe. Upon completion of the additions the reaction mixture was stirred at ambient temperature for about 90 minutes, then partitioned in ethyl acetate and water. The organic layer was separated and washed with aqueous 5% hydrochloric acid, then with aqueous saturated sodium chloride solution. The organic layer was dried with sodium sulfate and filtered. The filtrate was concentrated under reduced pressure to a residue, which was subjected to column chromatography on silica gel. Elution was accomplished with 5% ethyl acetate/heptane and 10% ethyl acetate/heptane as eluants. The product-containing fractions were combined and concentrated under reduced pressure, yielding 0.14 gram (82% yield) of 1-methyl-3-(2,5-dichloro-3-methoxyphenylmethyl)-6-trifluoromethyl-2,4(1H,3H)-pyrimidinedione, mp 124°–127° C. The NMR spectrum was consistent with the proposed structure.

I claim:

1. The compound 1-methyl-6-trifluoromethyl-2,4(1H,3H)-pyrimidinedione.

* * * * *